United States Patent
Worley et al.

(10) Patent No.: US 10,597,349 B2
(45) Date of Patent: *Mar. 24, 2020

(54) PROCESS FOR PURIFICATION OF METHYL METHACRYLATE

(71) Applicants: Rohm and Haas Company, Collegeville, PA (US); Dow Global Technologies LLC, Midland, MI (US)

(72) Inventors: William G. Worley, Missouri City, TX (US); Stacy W. Hoy, IV, Houston, TX (US)

(73) Assignees: Dow Global Technologies LLC, Midland, MI (US); Rohm and Haas Company, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/776,847

(22) PCT Filed: Dec. 7, 2016

(86) PCT No.: PCT/US2016/065324
§ 371 (c)(1),
(2) Date: May 17, 2018

(87) PCT Pub. No.: WO2017/105955
PCT Pub. Date: Jun. 22, 2017

(65) Prior Publication Data
US 2018/0346402 A1    Dec. 6, 2018

Related U.S. Application Data

(60) Provisional application No. 62/269,458, filed on Dec. 18, 2015.

(51) Int. Cl.
*B01D 3/14* (2006.01)
*B01D 3/36* (2006.01)
(Continued)

(52) U.S. Cl.
CPC .............. *C07C 67/54* (2013.01); *B01D 3/14* (2013.01); *B01D 3/36* (2013.01); *C07C 69/54* (2013.01)

(58) Field of Classification Search
CPC ...... B01D 3/14–40; C07C 67/54; C07C 69/54
See application file for complete search history.

(56) References Cited

U.S. PATENT DOCUMENTS

| 3,431,181 A | 3/1969 | Bouniot |
| 4,518,462 A | 5/1985 | Aoshima et al. |

(Continued)

FOREIGN PATENT DOCUMENTS

| CN | 103833551 A | 6/2014 |
| JP | 2582127 B2 | 2/1997 |
| JP | 3819419 B2 | 9/2006 |

OTHER PUBLICATIONS

Wu, et al., "Design and Control of a Methyl Methacrylate Separation Process with a Middle Decanter", Ind. Eng. Chem. Res, vol. 50, pp. 4595-4607 (2011).

*Primary Examiner* — Jonathan Luke Pilcher
(74) *Attorney, Agent, or Firm* — Brian L. Mutschler

(57) ABSTRACT

A process for purifying methyl methacrylate by feeding a product mixture comprising methanol, methyl methacrylate and alkali metal salts thereof, methacrolein, water and heavy byproducts to a distillation column having at least 15 trays. The product mixture and a $C_6$-$C_7$ hydrocarbon enter the distillation column above the middle of the distillation column. An overhead stream comprising $C_6$-$C_7$ hydrocarbon, methacrolein, methanol, water and methyl methacrylate and a bottoms stream comprising water, methyl methacrylate and its alkali metal salt and heavy byproducts are removed from the column.

9 Claims, 1 Drawing Sheet

(51) Int. Cl.
 *C07C 67/54* (2006.01)
 *C07C 69/54* (2006.01)

(56) References Cited

U.S. PATENT DOCUMENTS

| | | | |
|---|---|---|---|
| 5,028,735 A | | 7/1991 | Segawa et al. |
| 5,435,892 A | | 7/1995 | Miyazaki et al. |
| 10,301,251 B2 * | | 5/2019 | Groemping .............. C07C 45/28 |
| 2017/0354900 A1 * | | 12/2017 | Imazu ..................... C07C 51/44 |
| 2018/0251419 A1 * | | 9/2018 | Groemping ............. C07C 45/28 |
| 2018/0346403 A1 * | | 12/2018 | Worley ................... C07C 29/80 |

* cited by examiner

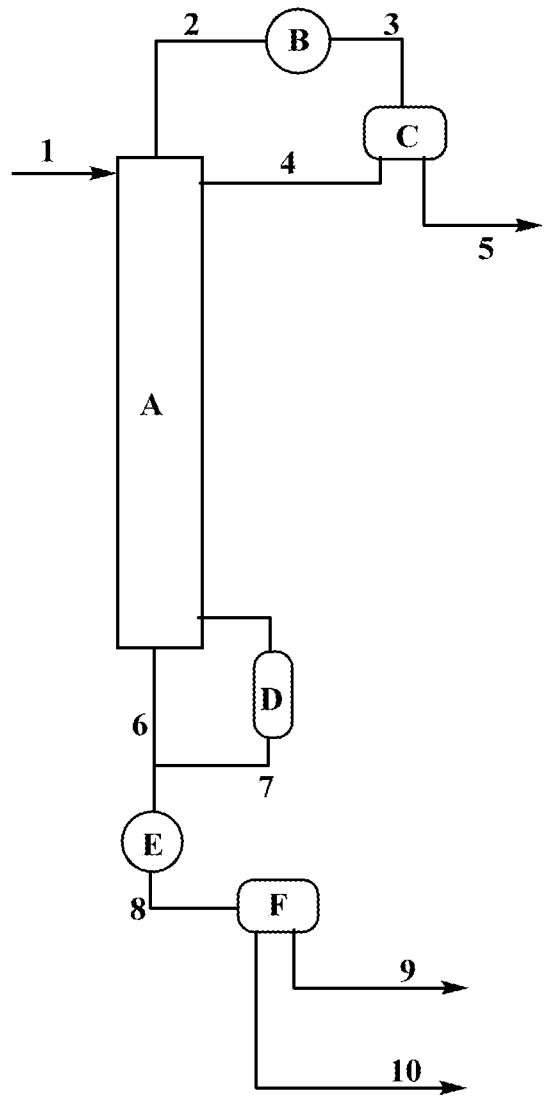

PROCESS FOR PURIFICATION OF METHYL METHACRYLATE

BACKGROUND OF THE INVENTION

The invention relates to a process for purification of a methyl methacrylate (MMA) reaction product from the effluent of an oxidative esterification reactor (OER).

The use of oxidative esterification to prepare MMA from methacrolein and methanol is well known. For example, U.S. Pat. No. 4,518,462 discloses a process having a methanol recovery column using hexane as an entrainer. However, this process is not suitable for reaction products which contain MMA salts. There is a need for a more efficient process for separating the components of reaction products resulting from preparation of methyl methacrylate.

SUMMARY OF THE INVENTION

The present invention is directed to a process for purifying methyl methacrylate; said method comprising: (a) feeding a reaction product mixture comprising methanol, methyl methacrylate and alkali metal salts thereof, methacrolein, water and heavy byproducts to a distillation column having at least 15 trays; wherein said reaction product mixture and a $C_6$-$C_7$ hydrocarbon enter the distillation column above the middle of the distillation column; (b) removing an overhead stream comprising $C_6$-$C_7$ hydrocarbon, methacrolein, methanol, water and methyl methacrylate; and (c) removing a bottoms stream comprising water, methyl methacrylate and its alkali metal salt and heavy byproducts.

BRIEF DESCRIPTION OF THE DRAWING

The FIGURE is a schematic of a process of the invention.

DETAILED DESCRIPTION OF THE INVENTION

All percentage compositions are weight percentages (wt %), and all temperatures are in ° C., unless otherwise indicated. Heavy byproducts are byproducts of the OER which have higher boiling points than methyl methacrylate, and which comprise oligomers of methyl methacrylate in addition to unknown products. Oligomers of methyl methacrylate comprise the dimer of methyl methacrylate and smaller amounts of higher oligomers, including, e.g., the trimer. Preferably, alkali metal salts are sodium or potassium salts, preferably sodium.

The $C_6$-$C_7$ hydrocarbon functions as an entrainer. It is believed that it breaks the methanol/MMA azeotrope, allowing removal and recovery of methanol. Preferably, the $C_6$-$C_7$ hydrocarbon is aliphatic. Preferably, the $C_6$-$C_7$ hydrocarbon is a saturated hydrocarbon, preferably an acyclic alkane. In one preferred embodiment, a mixture of $C_6$-$C_7$ hydrocarbons is used. Preferably, the $C_6$-$C_7$ hydrocarbon or mixture thereof has an atmospheric pressure (101 kPa) boiling point from 65 to 100° C., preferably at least 67° C.; preferably no greater than 90° C., preferably no greater than 80° C., preferably no greater than 75° C. Preferably, the $C_6$-$C_7$ hydrocarbon is n-hexane.

Preferably, the distillation column has at least 20 trays, preferably at least 25; preferably no more than 40 trays, preferably no more than 35 trays. Preferably, the point at which the reaction product mixture enters the distillation column is in the highest 40% of the trays, preferably the highest 30%, preferably the highest 20%, preferably the highest 10%, preferably the highest 7%. Preferably, the point at which the reaction product mixture enters the distillation column is in the highest ten trays, preferably in the highest eight trays, preferably in the highest six trays, preferably in the highest four trays, preferably in the highest three trays, preferably in the highest two trays, preferably in the top tray. Preferably, the reaction product mixture comprises at least 0.8 wt % methyl methacrylate alkali metal salts, preferably at least 1 wt %, preferably at least 1.5 wt %, preferably at least 1.8 wt %; preferably no more than 3 wt %, preferably no more than 2.5 wt %, preferably no more than 2 wt %. Preferably, the reaction product mixture comprises from 40 to 80 wt % methanol, preferably from 45 to 70 wt %, preferably from 50 to 68 wt %. Preferably, the reaction product mixture comprises from 5 to 40 wt % methyl methacrylate, preferably from 10 to 35 wt %, preferably from 15 to 32 wt %. Preferably, the reaction product mixture comprises from 1 to 10 wt % water, preferably from 3 to 9 wt %, preferably from 4 to 8 wt %. Preferably, the amount of the $C_6$-$C_7$ hydrocarbon(s) which enters the column as reflux is from 2 to 10 times the amount of methanol in the product mixture, preferably 3 to 5 times. Preferably, when additional $C_6$-$C_7$ hydrocarbon needs to be added, it enters the distillation column in the highest ten trays, preferably in the highest eight trays, preferably in the highest six trays, preferably in the highest four trays, preferably in the highest three trays, preferably in the highest two trays, preferably in the top tray.

In a preferred embodiment, prior to the process described herein, the direct product from the OER passes through a separate distillation column to remove light components, i.e., those having higher vapor pressure than methanol. The light components principally comprise methyl formate. Typical levels of methyl formate in the direct product are from 1 to 6 wt % and the reaction product mixture fed to the distillation column in the method of this invention typically contains no more than 1 wt % methyl formate.

The overhead stream passes through a condenser and then enters a water separator, from which the organic phase is returned to the same section of the distillation column where the product mixture enters, and the aqueous phase is removed. Preferably, water is added to the water separator. Preferably, the amount of water added to the water separator is 0.2 to 1 times the amount of the overhead stream, preferably 0.25 to 0.6 times Preferably, the bottoms stream enters a water separator after passing through a heat exchanger to cool it. The organic phase is predominantly MMA and preferably is processed further to obtain high-purity MMA. The aqueous phase contains methyl methacrylate alkali metal salt and water.

Water may be decanted from the stream by the means of standard methods. In one preferred embodiment, by means of a vessel that contains a vertical baffle or a series of baffles and is sized sufficiently that the organic and aqueous phase separate into individual phases. The lighter phase organic proceeds over the vertical baffle and the heavier water phase flows underneath the baffle. The separated liquids are withdrawn from the sections of the vessel that have accumulated the overflow and underflow of each phase.

The temperature and pressure in the distillation column is dependent on the composition of the material being distilled. In a preferred embodiment of the invention, the column is operated at reduced pressure, such as from about 100 to about 760 mmHg (13 to 101 kPa), or from 200 to 400 mmHg (26 to 53 kPa). Preferably, the column pressure is adjusted to keep the bottoms temperature below 120° C., preferably below 100° C.

Preferably, polymerization inhibitor is added to the column to minimize polymerization of MMA. Preferably, inhibitor is added above the middle of the column, preferably in the reflux. Amounts of inhibitor typically are small and types and typical use amounts are well known in the field.

The type of distillation column can be selected according to criteria well known to those skilled in the art.

The FIGURE depicts a distillation column A into which the product mixture 1 is introduced into the column. Bottoms, 6 from the column are split, with stream 8 passing through a heat exchanger E, with organic stream 9 and aqueous stream 10 removed from the column and recycle 7 returned to the column through reboiler D. Overhead stream 2 leaves the column at the top and passes through condenser B and the resulting stream 3 enters splitter C, with aqueous phase 5 removed from the column and organic phase 4 returned to the column.

EXAMPLES

Example 1

This experiment is carried out using the process configuration shown in FIG. 1. The distillation column is a 28 mm i.d. 30-tray Oldershaw column, and n-hexane is employed as the entrainer solvent. A steam-heated thermosiphon reboiler is used to provide the boil-up in the column. The pressure at the top of the column is 700 mmHg absolute. The overhead temperature is 48° C., and the bottoms temperature is 83° C.

A mixture containing 29.9% MMA, 58.1% methanol, 2.1% methacrolein, 7.1% water, and 1.2% sodium methacrylate, with the balance being lights (higher vapor pressure than methanol) and organic heavies (lower vapor pressure than MMA) is fed through line 1 at a rate of 197 g/hr to the top tray of the distillation column.

Surprisingly, no salt precipitation is observed on the trays or in the reboiler after 8 hours of run time. No sodium methacrylate is detected in the bottoms organic crude MMA stream so, further downstream processes will have no difficulty with salt precipitation.

TABLE 1

Stream Compositions and Process Conditions for Ex. 1

| Component | Line # 1 | 3 | 6 | 7 | 8 | 11 | 12 |
|---|---|---|---|---|---|---|---|
| Water | 7.10% | | 99.96% | 0.0% | 61.1% | 1.2% | 84.40% |
| Methanol | 58.10% | 99% | | 0.2% | 36.7% | | |
| Methacrolein | 2.10% | | | 1.6% | 0.7% | | |
| Methyl Methacrylate | 29.90% | | | 8.4% | 1.1% | 97.0% | 1.40% |
| Sodium Methacrylate | 1.20% | | | | | trace | 14.10% |
| Hexane | | | | 89.50% | | | |
| Phenothiazine | | 1% | | NA | NA | NA | NA |
| 4-Hydroxy Tempo | 0.04% | | 0.04% | NA | NA | NA | NA |
| Flow (g/hr) | 197.0 | 5.0 | 187.8 | 371.5 | 315.0 | 58.1 | 16.8 |

NA—not applicable

Example 2

An ASPEN simulation of feed location in a 30-tray distillation column (tray 1 is the top tray), assuming 60% tray efficiency produced the following results for the % MMA recycled to the column.

| Feed Tray | % MMA Recycled |
|---|---|
| 1 | 5.6% |
| 6 | 7.3% |
| 11 | 7.4% |
| 16 | 8.0% |
| 21 | 9.8% |

The efficiency of the column increases as the location of the reaction product mixture feed rises in the column.

The invention claimed is:

1. A process for purifying methyl methacrylate; said method comprising: (a) feeding a reaction product mixture comprising methanol, methyl methacrylate and alkali metal salt thereof, methacrolein, water and heavy byproducts to a distillation column having at least 15 trays; wherein said reaction product mixture and a $C_6$-$C_7$ hydrocarbon enter the distillation column above the middle of the distillation column; (b) removing an overhead stream comprising $C_6$-$C_7$ hydrocarbon, methacrolein, methanol, water and methyl methacrylate; and (c) removing a bottoms stream comprising water, methyl methacrylate and its alkali metal salt and heavy byproducts.

2. The process of claim 1 wherein the reaction product mixture comprises at least 0.8 wt % of a sodium salt of methyl methacrylate.

3. The process of claim 2 wherein the reaction product mixture comprises from 1 to 10 wt % water.

4. The process of claim 3 wherein the reaction product mixture enters the distillation column in the highest 30% of the trays.

5. The process of claim 4 wherein $C_6$-$C_7$ hydrocarbon is a saturated hydrocarbon having an atmospheric pressure boiling point from 65 to 100° C.

6. The process of claim 5 wherein a portion of the overhead stream returns to the distillation column in the highest 30% of the trays and the amount of the $C_6$-$C_7$ hydrocarbon in said portion of the overhead stream which enters the column is from 2 to 10 times the amount of methanol in the reaction product mixture.

7. The process of claim 6 wherein the reaction product mixture enters the distillation column in the highest 20% of the trays.

8. The process of claim 7 wherein the distillation column has from 20 to 40 trays.

9. The process of claim 8 wherein the reaction product mixture enters the distillation column in the highest four trays.

\* \* \* \* \*